United States Patent [19]
Van Driel

[11] Patent Number: 6,050,968
[45] Date of Patent: Apr. 18, 2000

[54] TWO-CHAMBERED SOFTSHELL RESERVOIR

[75] Inventor: Michael R. Van Driel, Fountain Valley, Calif.

[73] Assignee: Medtronic, Inc., Minneapolis, Minn.

[21] Appl. No.: 08/939,383

[22] Filed: Sep. 29, 1997

[51] Int. Cl.[7] ............................. A61M 37/00; A61M 1/14
[52] U.S. Cl. .................................................. 604/4; 422/44
[58] Field of Search .................................... 604/410, 320, 604/5, 6; 422/44

[56] References Cited

U.S. PATENT DOCUMENTS

| | | | |
|---|---|---|---|
| 3,890,969 | 6/1975 | Fischel | 128/214 R |
| 3,892,534 | 7/1975 | Leonard | 23/258.5 |
| 3,911,918 | 10/1975 | Turner | 128/272 |
| 3,915,650 | 10/1975 | Talonn | 23/258.5 |
| 4,026,669 | 5/1977 | Leonard et al. | 23/258.5 R |
| 4,602,910 | 7/1986 | Larkin | 604/87 |
| 4,734,269 | 3/1988 | Clarke et al. | 422/310 |
| 4,737,139 | 4/1988 | Zupkas et al. | 604/4 |
| 4,969,882 | 11/1990 | Carmen et al. | 604/410 |
| 5,049,146 | 9/1991 | Bringham et al. | 604/4 |
| 5,061,236 | 10/1991 | Sutherland et al. | 604/4 |
| 5,158,533 | 10/1992 | Strauss et al. | 604/4 |
| 5,411,705 | 5/1995 | Thor et al. | 422/45 |
| 5,573,526 | 11/1996 | Hess | 604/408 |
| 5,830,198 | 11/1998 | Henniges et al. | 604/320 |

FOREIGN PATENT DOCUMENTS

| | | | |
|---|---|---|---|
| 2584608 | 7/1985 | France | A61M 1/14 |

*Primary Examiner*—Ronald Stright
*Assistant Examiner*—Cheryl L. Huseman
*Attorney, Agent, or Firm*—Harry G. Weissenberger

[57] ABSTRACT

A softshell blood reservoir for heart-lung machines is symmetrical about a central vertical axis and is divided into two chambers: a small main chamber accessed by the blood inlet and outlet connectors, and a larger storage chamber accessed from the main chamber through a selectably closable passage. This arrangement greatly reduces the priming volume of the reservoir without substantially affecting its total capacity, and enhances the mixing of venous and cardiotomy blood.

7 Claims, 2 Drawing Sheets

TWO-CHAMBERED SOFTSHELL RESERVOIR

FIELD OF THE INVENTION

This invention relates to softshell blood reservoirs for cardiac surgery, and more particularly to a symmetrical two-chambered reservoir which substantially reduces the need for saline priming and improves mixing of cardiotomy and venous blood.

BACKGROUND OF THE INVENTION

Softshell reservoirs are commonly used in cardiac surgery to mix venous blood and cardiotomy blood in a heart-lung machine circuit. Prior to the surgery, the blood circuit including the softshell reservoir has to be primed with saline solution so that all air in the circuit is removed, and the circulation through the heart-lung machine can instantly be substituted for the natural circulation. When the patient is switched to the heart-lung machine, the saline solution used for priming mixes with the patient's blood and dilutes it. This is physiologically undesirable not only because it makes the blood supply to the patient temporarily non-homologous, but because it produces symptoms of anemia that keep the patient weak and listless for several days after the surgery until the body rebuilds a sufficient concentration of blood cells.

It is therefore important to minimize the priming volume of the blood circuit in the heart-lung machine. Perfusionists are conscious of that problem and attempt to alleviate it by choosing low prime oxygenators and filters, and by minimizing the length of the tubing interconnecting the components of the blood circuit. A major factor in the priming problem is the softshell reservoir bag. This bag typically holds about 800–1300 ml of fluid. To prime it, the entire bag must be wetted out, thereby requiring a priming volume in excess of 1 liter of saline solution. It would thus be highly desirable to provide a softshell reservoir which has a similar capacity but which requires substantially less priming volume.

Another problem of conventional softshell reservoirs is the occurrence of stagnation areas and incomplete mixing of cardiotomy and venous blood. This is due to the asymmetrical design of conventional softshell reservoirs, in which the cardiotomy and venous inlets are typically on one side of the reservoir's central vertical axis, and the outlet is on the other side. Because both the inlets and the outlet enter the conventional bag in a vertical direction at the bottom of the reservoir, this results in different path legths and configurations for the cardiotomy path and the venous path. These differences produce the above-mentioned problems.

SUMMARY OF THE INVENTION

The present invention considerably reduces the priming volume of a softshell reservoir without significantly reducing its capacity by forming the reservoir with two vertically-spaced sections or chambers that are symmetrical about a central vertical axis and are connected by a short conduit that can be closed off by a clamp. The lower section is a small main chamber, which is part of the blood circuit and needs to be primed. The upper section is a larger storage chamber into which blood can be temporarily diverted during the operation of the heart-lung machine when additional capacity is required. The main chamber has the shape of an inverted funnel to direct any trapped microair toward the storage reservoir. The storage chamber is also funnel-shaped but right-side up to prevent stagnation of blood as the storage reservoir fills and empties.

The reservoir of this invention is also symmetrical about a central vertical axis. The outlet is at the bottom of the main chamber on the central axis, while the two inlets are near the top of the main chamber and are equally spaced from the central axis on opposite sides thereof. This equalizes the cardiotomy and venous paths and assures the effective mixing of cardiotomy and venous blood as they flow toward the outlet. The symmetrical construction of the softshell reservoir also allows the bilateral connectability of the cardiotomy and venous lines as described and claimed in the copending application Ser. No. 08/939,382 entitled "Bilaterally Connectable Softshell Reservoir" filed on even date herewith.

DESCRIPTION OF THE PREFERRED EMBODIMENT

Figure 1:
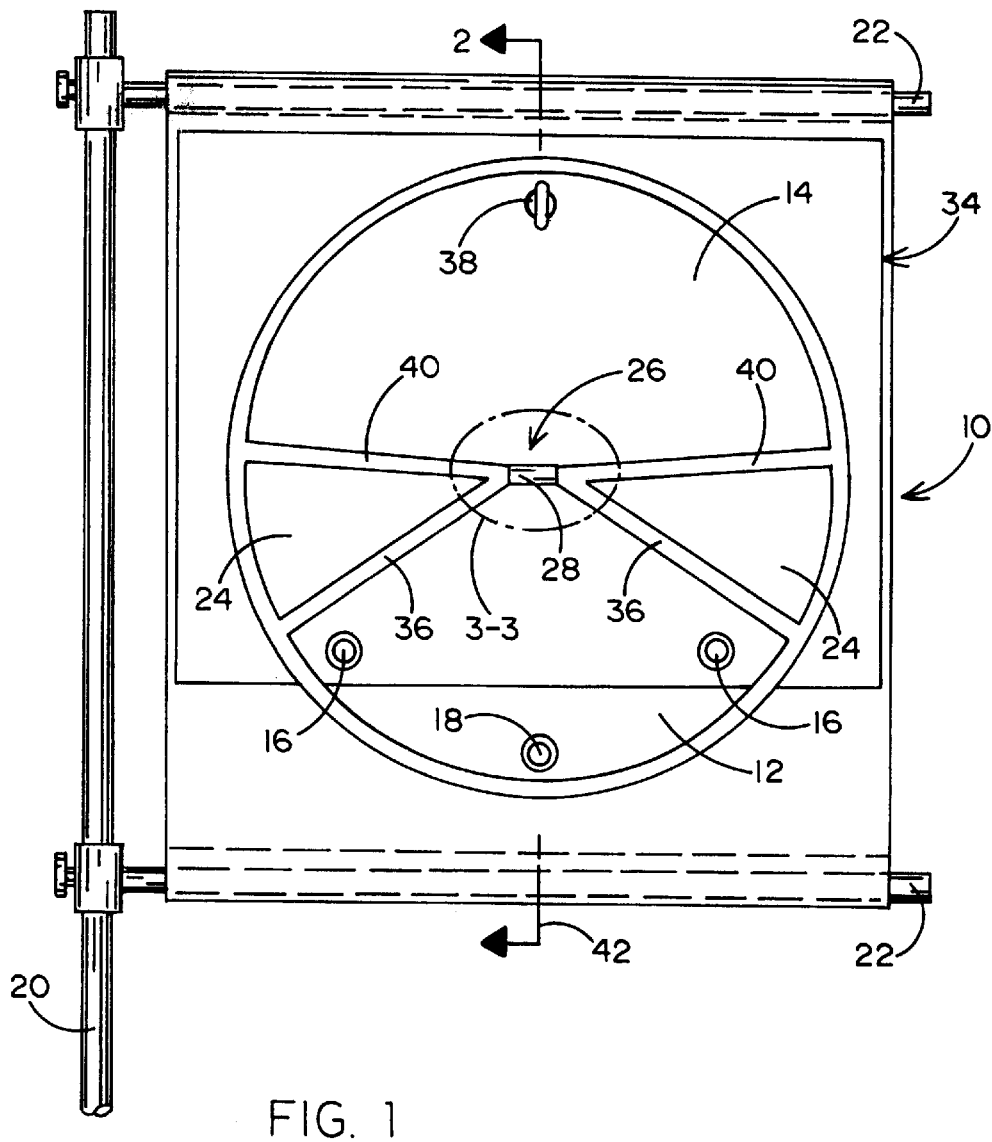
FIG. 1 is a front elevation of the reservoir of this invention.
Figure 3:
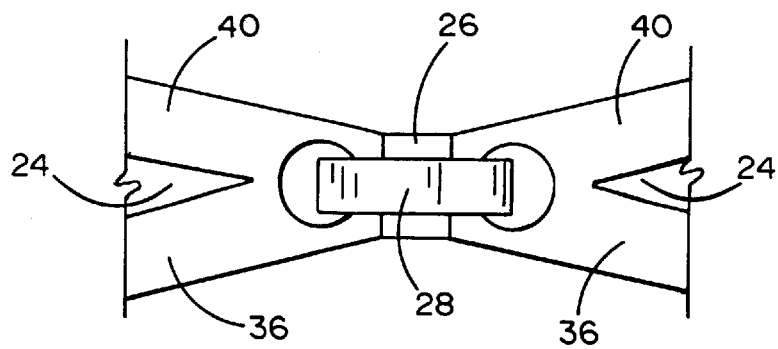
FIG. 3 is a detail elevation of the reservoir along line 3—3 of FIG. 1.

As shown in FIG. 1, the softshell reservoir 10 of this invention is composed of a small main chamber 12 and a larger storage chamber 14. Blood inlets 16 for venous and cardiotomy blood, as well as a blood outlet 18, are formed on the main chamber 12 and communicate therewith. The softshell reservoir 10 is conventionally mounted on a support 20 by arms 22 when in use.

The chambers 12 and 14 are separated by pie-wedge-shaped noninflatable separators 24, but are connected by a passage 26 that is normally squeezed shut but can be opened by releasing the tubing clamp 28. The reservoir 10 is formed by radio-frequency welding two flat plastic sheets 30, 32 (FIG. 2) under pressure, with an interposed bubble screen 34 having a pore diameter of 1–3.5 μm, in all areas except the chambers 12 and 14. Prior to use, the softshell reservoir 10 is completely flat, and the chambers 12, 14 have zero internal volume.

Figure 2:
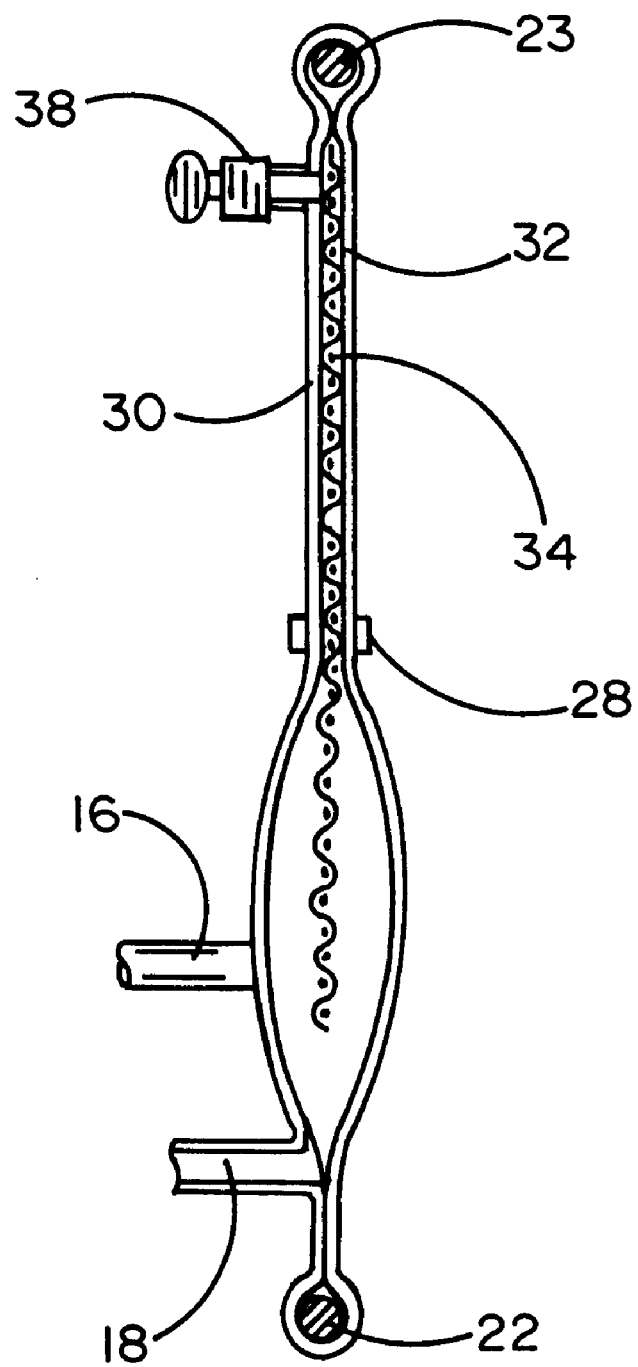
FIG. 2 is a vertical section along line 2—2 of FIG. 1 during priming.

In use, the softshell reservoir 10 is suspended on the support 20, and the blood inlets 16 are connected to a source of venous blood and filtered cardiotomy blood, respectively. The blood outlet 18 is connected to the pump (not shown) of a heart-lung machine. With the passage 26 closed, the main chamber 12 is now primed by introducing saline solution through the inlets 16. The elasticity of the reservoir material allows the chamber 12 to bulge as shown in FIG. 2 and receive between 50 and 400 ml of priming saline.

During the surgery, the blood influx through the inlets 16 will at times exceed, and at other times fall short of, the blood outflow drawn by the heart-lung machine pump through the outlet 18. Therefore, when the main chamber 12 becomes filled with blood as the surgery begins, the perfusionist releases the clamp 28, and additional temporary blood storage on the order of 500–600 ml becomes available in the storage chamber 14 until the total capacity (about 550–1200 ml) of the reservoir 10 is reached. Because the mixing of venous and cardiotomy blood takes place in the small main chamber 12, faster and more thorough mixing is accomplished in the inventive reservoir 10 than in prior art single-chamber softshell reservoirs.

The inwardly upward inclination of the walls 36 of the main chamber 12 causes any microair bubbles in the blood which adhere to the bubble screen 34 to migrate toward the passage 26 and upward into the storage chamber 14 when the reservoir is gently tapped by the perfusionist. Any accumulated air in the chamber 14 can be drained by opening the stopcock 38. The inwardly downward inclination of the walls 40 directs stored blood from the lateral sides of chamber 14 toward the passage 26 when blood is drained from storage, so as to prevent any stagnation of blood in the storage chamber 14 which might cause clotting.

It will be noted that the reservoir 10 is completely symmetrical with respect to the central vertical axis 42, and that the two inlets 16 are equally spaced from the central axis 42 on opposite sides thereof. This assures effective and even mixing of the cardiotomy and venous blood in the main chamber 12, and an even, non-stagnant flow into and out of the storage chamber 14.

It is understood that the exemplary two-chambered softshell reservoir described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A softshell blood reservoir for storing venous blood in an extracorporeal cardiopulmonary circuit, comprising:

a) a main chamber having a blood inlet and a blood outlet connected thereto to convey blood through said main chamber;

b) a storage chamber having a selectively openable air outlet but communicating only with said main chambers to convey blood to and from said main chamber;

c) a selectable openable fluid passage interconnecting said main chamber and said storage chamber; and d) a releasable closure member arranged to close said passage when interconnection between said chambers is not desired.

2. The reservoir of claim 1, in which said main chamber is positioned below said storage chamber.

3. The reservoir of claim 2, in which the upper walls of said main chamber are upwardly inwardly inclined toward said passage to direct microair in said main chamber toward said passage.

4. The reservoir of claim 2, in which the lower walls of said storage chamber are downwardly inwardly inclined toward said passage to prevent blood stagnation when draining blood from said storage chamber into said main chamber.

5. The reservoir of claim 1, in which the blood volume capacity of said main chamber is smaller than that of said storage chamber.

6. The reservoir of claim 1, further comprising a bubble screen vertically disposed through both of said chambers.

7. The reservoir of claim 1, in which said reservoir is symmetrical about its central vertical axis.

* * * * *